(12) United States Patent
Ossikovski et al.

(10) Patent No.: US 7,859,661 B2
(45) Date of Patent: Dec. 28, 2010

(54) POLARIMETRIC RAMAN SYSTEM AND METHOD FOR ANALYSING A SAMPLE

(75) Inventors: Razvigor Ossikovski, Villebon sur Yvette (FR); Antonello De Martino, Massy (IT); Bernard Drevillon, Clamart (FR)

(73) Assignees: Ecole Polytechnique, Palaiseau (FR); Centre National de la Recherche Scientifique, Paris (FR)

( * ) Notice: Subject to any disclaimer, the term of this patent is extended or adjusted under 35 U.S.C. 154(b) by 137 days.

(21) Appl. No.: 12/158,323

(22) PCT Filed: Jan. 19, 2007

(86) PCT No.: PCT/EP2007/050547
§ 371 (c)(1),
(2), (4) Date: Aug. 6, 2008

(87) PCT Pub. No.: WO2007/082937
PCT Pub. Date: Jul. 26, 2007

(65) Prior Publication Data
US 2008/0304061 A1      Dec. 11, 2008

(30) Foreign Application Priority Data
Jan. 20, 2006    (EP)  .................. 06300050

(51) Int. Cl.
*G01J 3/44*      (2006.01)
*G01N 21/65*      (2006.01)
(52) U.S. Cl. .................. 356/301; 356/369
(58) Field of Classification Search .................. 356/301
See application file for complete search history.

(56) References Cited

U.S. PATENT DOCUMENTS

| 6,175,412 | B1 | 1/2001 | Drevillon et al. |
| 6,975,397 | B2 | 12/2005 | Hug |

(Continued)

FOREIGN PATENT DOCUMENTS

EP        0 190 628 A2     8/1986

(Continued)

OTHER PUBLICATIONS

Hecht et al., "Raman Optical Activity Instrument for Studies of Biopolymer Structures and Dynamics," J. of Raman Spectr., vol. 30, No. 9, pp. 815-825 (1999).

(Continued)

*Primary Examiner*—F. L Evans
(74) *Attorney, Agent, or Firm*—Young & Thompson

(57) ABSTRACT

A Raman method and system for analysing a sample including an excitation source emitting an incident light beam, a sample holder for mounting the sample, elements for focusing the incident light beam onto the sample surface to generate a Raman scattered light having an intensity, elements for collecting the Raman scattered light to form a Raman scattered light beam, a detection system measuring intensity of the Raman scattered light beam as a function of time. The system includes at least a polarization state generator able to generate four independent polarization states or a polarization state analyzer able to analyze four independent polarization states to detect the intensity of the Raman scattered light beam and calculate a partial or complete Mueller-Stokes matrix of the sample.

13 Claims, 6 Drawing Sheets

U.S. PATENT DOCUMENTS

2003/0106492 A1  6/2003  Levinson et al.
2004/0130717 A1  7/2004  Drevillon et al.

FOREIGN PATENT DOCUMENTS

WO  2006/029604 A1  3/2006

OTHER PUBLICATIONS

Loechelt et al., "Polarized Off-axis Raman Spectroscopy: A Technique for measuring stress tensors in semiconductors," J. of Appl. Phys., vol. 86, No. 11, pp. 6164-6180 (Dec. 1, 1999).

De Martino et al., "General methods for optimized design and calibration of Mueller polarimeters," Thin Solid Films, vol. 455-456, pp. 112-119 (May 1, 2004).

Garcia-Caurel et al., "Spectroscopic Mueller polarimeter based on liquid crystal devices," Thin Solid Films, vol. 455-456, pp. 120-123 (May 1, 2004).

Poborochii et al., "Subwavelength-Resolution Raman Microscopy of Si structures Using Metal-Particle-Topped AFM Probe," Jap. J. of Appl. Phys., vol. 44, No. 6, pp. 202-204 (2005).

POLARIMETRIC RAMAN SYSTEM AND METHOD FOR ANALYSING A SAMPLE

The invention concerns a Polarimetric Raman system and method for analysing a sample.

As an example, non-destructive characterization of the mechanical stress induced in the semiconductor microstructures during their processing is of crucial importance for modern VLSI microelectronic industry.

The common procedure for the characterization of stress present in crystalline materials uses the frequency shifts, induced by the strain, of the Raman active modes under observation [I. de Wolf, Semicond. Sci. Technol. 11, 139 (1996)].

In the particular case of silicon structures, it is the triply degenerate phonon peak at 521 cm$^{-1}$ that is monitored. The strain present in the structure lifts the degeneracy by shifting the three frequencies $\omega_k$, k=1, 2, 3 of the three Raman phonon modes from their initial common value $\omega_0$=521 cm$^{-1}$, as well as by modifying the three corresponding Raman tensors $R_k$ [E. Anastassakis, in *Light Scattering in Semiconductor Structures and Materials*, p. 173 (D. J. Lockwood and J. F. Young eds., Plenum, New York, 1991)].

While all procedures proposed are based on the analysis of the frequency shifts of the Raman modes, only few have exploited so far the additional information provided by the Raman tensor modifications [G. H. Loechelt, N. G. Cave and J. Menéndez, J. Appl. Phys. 86, 6164 (1999)].

The measurement of only three frequency shifts imposes the use of simplifying hypotheses on the symmetry properties of the stress tensor σ, generally having six independent components, in order to reduce the number of unknown parameters.

By using conventional Raman method, it is not possible to fully characterize the modified Raman tensors and therefore, to achieve complete determination of the stress tensor σ without the need for hypotheses on its symmetry properties.

The Raman scattering configuration containing a polarizer in the incident beam and an analyser in the scattered beam is the most commonly used one in conventional Raman spectroscopy (together with its "reduced" implementations using only a polarizer or an analyser), see FIG. 1. This configuration is generally referred to as polarized (or "depolarized", if the analyser is absent) Raman spectroscopy [D. A. Long, *Raman Spectroscopy*, pp. 28; 126; 120 (McGraw Hill, New York, 1977)]. The intensity response in polarized (or depolarized) Raman is conveniently described within the Placzek formalism, aftermentioned.

FIG. 1 represents a general configuration of a polarized Raman scattering experiment. The polarized Raman system comprises an excitation source 1 emitting an incident light beam 2 and a sample holder 3, on which the sample 4 can be mounted. The incident light beam 2 is focused on the sample 4 to generate a Raman scattered light.

It comprises optics to focus the incident light beam 2 onto the sample surface 16 as well as to collect the Raman scattered light to form a Raman scattered light beam 5.

It comprises a detection system 6 measuring the intensity of the Raman scattered light beam 5 as a function of time.

The polarizer 17 may be replaced by a polarization rotator (a half-wave plate) if the incident light beam 2 is naturally polarized. Likewise, the analyser 18 may be absent ("depolarized configuration").

In the case of some non-conventional Raman experiments, such as the measurement of the natural or induced Raman optical activity (ROA), besides the polarizer 17 and the analyser 18 in the incident 2 and scattered 5 beams respectively, there may be other polarization components present in one or in both beams, see FIG. 2.

ROA measurements are generally applied to chiral molecules in aqueous solution like biopolymers.

In ROA measurement configurations, optical components generating alternatively right and left circular polarization states, such as Pockels cell modulators [L. D. Barron, M. P. Bogaard and A. D. Buckingham, J. Am. Chem. Soc. 95, 603 (1973)] or quarter-wave plates periodically switched between two given mechanical azimuths [K. M. Spencer, T. B. Freedman and L. A. Nafie, Chem. Phys. Lett. 149, 367 (1988)], are inserted in the incident and/or in the scattered beam. Also, there may be a depolarizer present in the scattered beam [L. Hecht, L. D. Barron, E. W. Blanch and A. F. Bell, L. A. Day, J. Raman Spectrosc. 30, 815 (1999)], instead of the analyser.

FIG. 2 represents a typical configuration of a ROA experiment. A two-state optical modulator (TSOM) 19 is inserted between the polarizer 17 and the sample 4. The polarizer 17 may be replaced by a polarization rotator (a half-wave plate) if the incident light beam 2 is naturally polarized. A depolarizer may be replacing the analyser 18 in certain configurations. Also, there may be a TSOM 19 in the scattered beam 5 instead of in the incident beam 2 or there may be two TSOM 19, one in each beam.

Now at least one of the polarization states is no more linear (as was the case with the use of the polarizer and the analyser alone) but circular. The description of ROA experiments is much more natural within the framework of the Mueller-Stokes formalism, aftermentioned [L. Hecht, B. Jordanov and B. Schrader, Appl. Spectrosc. 41, 295 (1987)].

The problem with polarized (or "depolarized") Raman or ROA systems is that it provides only partial information on the polarization characteristics of the sample.

The aim of the present invention consists to provide a polarimetric Raman system and method allowing determination of the complete polarization characteristics of a sample.

To this end, the invention concerns a polarimetric Raman system for analysing a sample comprising:
- an excitation source emitting an incident light beam, said excitation source being configured for producing a Raman scattered light having an intensity,
- a sample holder, on which the sample can be mounted,
- means for focusing the incident light beam onto the sample surface to generate the Raman scattered light,
- means for collecting the Raman scattered light and filtering it from Rayleigh scattered light to form a Raman scattered light beam,
- a detection system measuring intensity of the Raman scattered light beam as a function of time.

According to the invention, it comprises at least a polarization state generator (PSG) able to produce four independent polarization states or a polarization state analyser (PSA) able to analyse four independent polarization states in order to detect the intensity of the Raman scattered light beam making it possible to calculate a partial or complete Mueller-Stokes matrix of the sample, the incident light beam passing through said PSG before being scattered by the sample and the Raman scattered light beam passing through said PSA after being scattered by the sample.

According to various embodiments, the present invention also concerns the characteristics below, considered individually or in all their technical possible combinations:
  the Raman system comprises a PSG working with a PSA, said PSG being able to generate four independent polarization states and said PSA being able to analyse four independent polarization states making it possible to obtain a complete or partial Mueller-Stokes matrix of the sample comprising 16 elements, the Raman system comprises a beamsplitter located between the PSG and the sample, the incident light beam passing through said beamsplitter before being backscattered by the sample, generating a Raman backscattered light beam reflected by the beamsplitter before passing through the PSA, the Raman system comprises only a PSA, the Raman scattered light beam passing through said PSA after being scattered by the sample, the Raman system comprises a PSA and a polarizing component, the incident light beam passing through said polarizing component before being scattered by the sample and the Raman scattered light beam passing through said PSA after being scattered by the sample, the Raman system comprises a PSG and an analyser, the incident light beam passing through said PSG before being scattered by the sample and the Raman scattered light beam passing through said analyser after being scattered by the sample, the Raman system comprises a sharp tip such a tip-enhanced Raman spectroscopy (TERS) sharp tip, said sharp tip being very close or in contact with the incident light spot at the surface of the sample and exciting the near-field contribution to the scattered Raman field transmitted to a recording means.

The present invention concerns a polarimetric Raman method for analysing a sample wherein:

an incident light beam adapted for producing a Raman scattered light having an intensity is generated, the incident light beam is focused onto the sample surface to generate the Raman scattered light, the Raman scattered light is collected and filtered from Rayleigh scattered light to form a Raman scattered light beam, intensity of the Raman scattered light beam is measured as a function of time.

According to the invention, four independent polarization states of the incident light beam before being scattered by the sample are generated and/or four independent polarization states of the Raman scattered light beam after being scattered by the sample are analysed in order to detect the intensity of the Raman scattered light beam making it possible to calculate a partial or complete Mueller-Stokes matrix of the sample.

According to various embodiments, the present invention also concerns the characteristics below, considered individually or in all their technical possible combinations:

four independent polarization states of the incident light beam are generated and in that four independent polarization states of the Raman scattered light beam are analysed consecutively for each independent polarization states of the incident light beam generated making it possible to obtain a complete or partial Mueller-Stokes matrix of the sample comprising 16 elements, the incident light beam passes through a beamsplitter before being backscattered by the sample, generating a Raman backscattered light beam, four independent polarization states of the Raman backscattered light beam being analysed after the reflection of the Raman backscattered light beam on the beamsplitter, the incident light beam totally or partially polarized before being scattered by the sample generates only one independent polarization state and in that up to four independent polarization states of the Raman scattered light beam are analysed after being scattered onto the sample, up to four independent polarization states of the incident light beam before being scattered by the sample are generated and in that only one independent polarization state of the Raman scattered light beam is analysed for each independent polarization state of the incident light beam, it is applied to tip-enhanced Raman spectroscopy (TERS) wherein the near-field contribution to the scattered Raman field is measured.

The description of the invention is illustrated by the following drawings in which.

Figure 1:
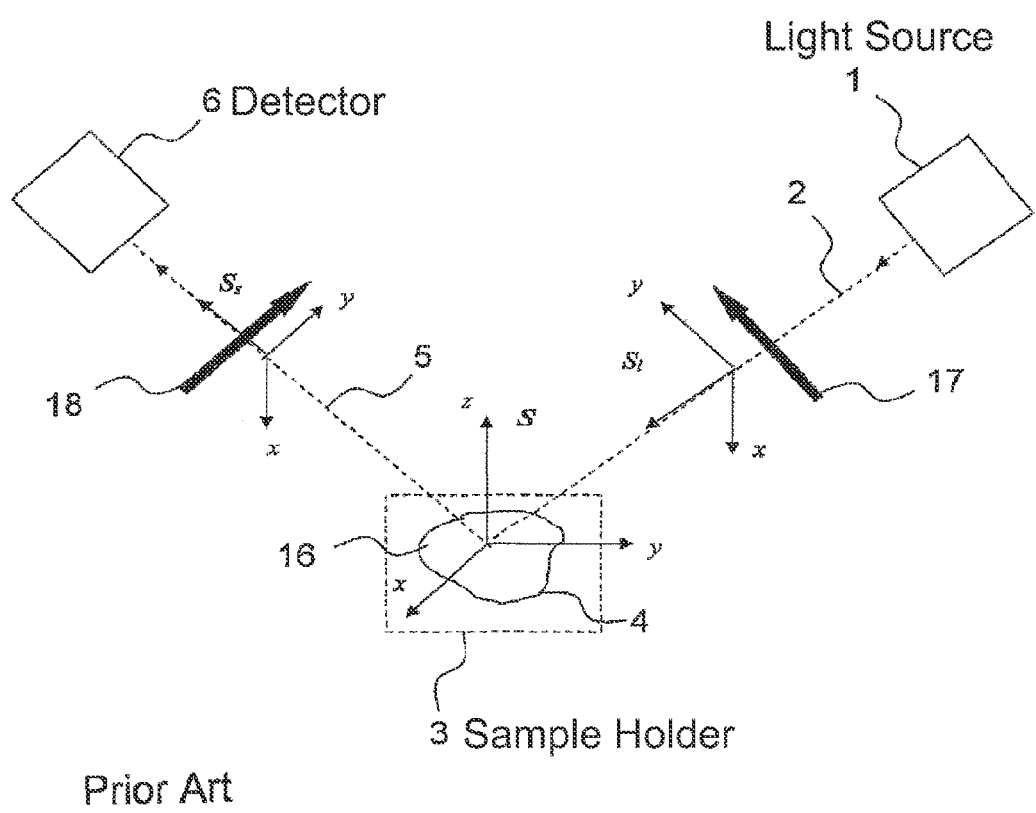
FIG. 1 represents a general configuration of a polarized Raman scattering system.
Figure 2:
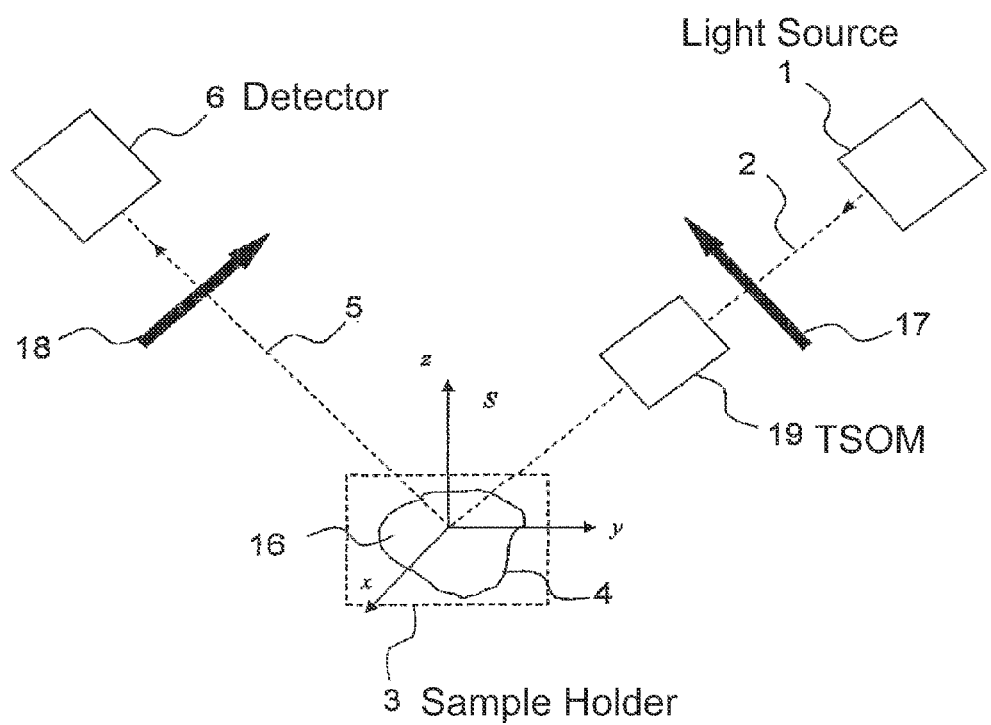
FIG. 2 represents a typical configuration of a ROA system

It comprises an excitation source 1 emitting an incident light beam 2 and a sample holder 3, on which the sample 4 can be mounted. The incident light beam 2 is focused on the sample 4 to generate a Raman scattered light.

The excitation source 1 is configured for producing a Raman scattered light having an intensity.

The excitation source 1 can be a laser emitting a monochromatic light beam which is very coherent with a well defined polarisation. The emitted light beam is a confined and non divergent beam It comprises optics to focus the incident light beam 2 onto the sample surface 16 as well as optics to collect the Raman scattered light and filter it from Rayleigh scattered light to form a Raman scattered light beam 5.

It comprises a detection system 6 measuring the intensity of the Raman scattered light beam 5 as a function of time.

The polarimetric Raman system can comprise at least a polarization state generator (PSG) 7 or a polarization state analyser (PSA) 8 able to generate four independent polarization states in order to detect the intensity of the Raman scattered light beam 5 making it possible to calculate a Mueller-Stokes matrix of the sample 4 and thus the complete polarization characteristics of the sample 4.

The Mueller-Stokes matrix comprising 16 elements can be completely or partially calculated. It depends of the number of independent polarization states generated or analysed.

Figure 3:
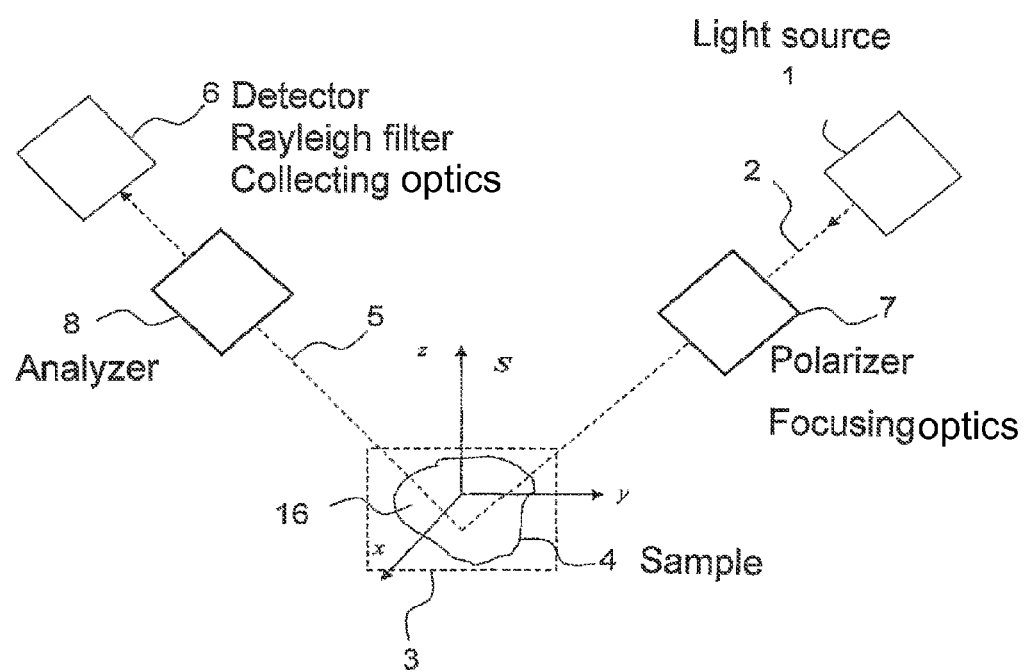
FIG. 3 represents a general configuration of the polarimetric Raman system according to one possible embodiment of the invention.

According to one possible embodiment of the invention on FIG. 3, the polarimetric Raman system comprises a PSG 7 and a PSA 8.

The incident light beam 2 passes through the PSG 7 before being scattered by the sample 4. And the Raman scattered light beam 5 passes through the PSA 8 after being scattered by the sample 4.

Such PSG 7 and PSA 8 (which is also called PSD (polarization state detector)) are described in the document US2004130717.

In a PSG, the light polarization can be modulated by a variety of devices such as discrete components inserted and then removed from the light path [Bickel W. S. et al.; Am. J. Phys 53 (1984) 468], rotating retardation plates [Goldstein D. H.; Appl. Opt. 31 (1992) 6676], rotating compensators [Collins R. W. and Koh J.; J. Opt. Soc. A 16, (1999) 1997], Pockels cells [Delplancke F.; Appl. Opt. 36 (1997) 5388 and Compain E. and Drévillon B.; Rev. Sci. Instrum. 68 (1997) 2671] or photoacoustic modulators [Compain E. and Drévillon B.; Rev. Sci. Instrum. 69, (1998) 1574].

For PSA, one can use the same devices and a single detector, or a "parallel" analysis of light polarization through polarization-sensitive beamsplitters and simultaneous measurement of the separated beams by several detectors [Azzam R. M. A., Opt. Acta 29 (1982) 685, Brudzewski K.; J. Modern Optics 38 (1991) 889, Khrishnan S.; J. Opt. Soc. Am A 9 (1992) 1615, Compain E. et al., Thin Solid Films 313 (1998)].

It is possible to use PSG and PSA including liquid crystal (LC) variable retarders. Two types of such devices are currently available. First, nematic liquid crystals (NLC) provide variable retardation with fixed orientation of slow and fast axes, with typical response times of the order of 10 to 100 ms. On the other hand ferroelectric liquid crystals (FLC) provide fixed retardation, but with slow and fast axis directions which can be electrically switched between two azimuthal angles separated by 45 [deg.], in times typically shorter than 100 [mu]s.

Such PSG or PSA comprises usually a linear polarizer and two liquid crystal modulators.

After reflection of the incident light beam 2 onto the sample 4, each one of the up to four independent polarization states that had been originally generated by the PSG 7, is successively analysed up to four times by the PSA 8, giving as a result 16 independent intensity measurements necessary for the determination of the Mueller-Stokes matrix of the sample 4.

The originality of the polarimetric Raman system is that it is the Raman frequency-shifted scattered radiation which is directly analysed by the PSA 8.

Formalisms of polarized and polarimetric Raman spectroscopy experiments are after-described.

The polarizations of the incident 2 and the scattered 5 light beams in Raman spectroscopy are important parameters of the experiment itself, as exemplified by Placzek formula [G. Placzek, in *Handbuch der Radiologie*, vol. VI, 2, p. 205 (E. Marx ed., Akademische Verlag, Leipzig, 1934)].

This relation lying in the basis of the quantitative analysis of the polarized Raman scattering experiment yields the total scattered intensity I given the polarization states of the incident and of the Raman scattered light and the Raman tensor, characteristic of the scattering medium. In its "crystalline material version" it reads [R. Loudon, Advan. Phys. 13, 423 (1964)]:

$$I = kI_0 \sum_k |e^{sT} R_k e^i|^2 \qquad (1)$$

with k being a proportionality constant, $I_0$ the intensity of the incident light, $e^i$ and $e^s$, three-dimensional unit vectors describing respectively, the polarization state of the incident light 2 and that of the Raman scattered light 5 along the direction of observation and $R_k$, the 3×3 Raman tensor of the k-th active Raman mode (or scatterer) observed (the superscript T stands for the matrix-vector transpose).

The general forms of the Raman tensors R have been tabulated for all classes of the crystal systems and all phonon modes.

In the case of amorphous or liquid materials, the sum over the phonon modes observed should be replaced by an ensemble space average $\langle ... \rangle$ over all possible orientations of the individual scatterers [L. A. Nafie and D. Che, in *Modern Non-linear Optics*, part 3, p. 105 (Advances in Chemical Physics Series, vol. LXXXV, M. Evans and S. Kielich eds., John Wiley & Sons, New York, 1994)]:

$$I = kI_0 \langle |e^{sT} R e^i|^2 \rangle \qquad (2)$$

It should be noted that there is a fundamental asymmetry between the vectors $e^s$ and $e^i$: while the incident polarization state $e^i$ is either "prepared" by a polarizer 17 inserted in the incident beam 2 or is naturally present because of the natural polarization of the exciting laser sources 1 currently used in Raman scattering experiments, $e^s$ is always imposed by an analyser 18 inserted in the scattered beam 5 perpendicularly to the direction of observation.

Thus, when both the polarizer 17 and the analyser 18 are present (or the incident beam 2 is naturally polarized without the use of the polarizer 17), the experiment is termed as polarized Raman spectroscopy as above described (FIG. 1).

If the analyser 18 is absent from the scattering configuration (case currently referred to as "depolarized" configuration; the term "unanalysed" being more correct), the Placzek formula (1) takes the form: (in the crystalline material case)

$$I = kI_0 \sum_k |R_k e^i|^2 \qquad (3)$$

A closer inspection of Eq. (1) shows that it can be rewritten in the equivalent form:

$$I = k \sum_k |e^{sT} R_k E^i|^2 \qquad (4)$$

where $E^i$ is the incident electric field. Further, the squared modulus can be interpreted as being the squared projection of the scattered electric field on the polarization state of the observation direction. This interpretation yields the following simple expression for the electric field $E^s$ scattered by a single scatterer described by its Raman tensor R given the incident field $E^i$:

$$E^s = RE^i \qquad (5)$$

By introducing two coordinate systems, $S_i$ and $S_s$ respectively for the incident 2 and scattered 5 light in such a way that the their z axes be directed along the light propagation direction, we may rewrite the above expression in the form:

$$v^s = Jv^i \qquad (6)$$

$S_i$, $S_s$ and S are the Cartesian coordinate systems of respectively, the incident beam 2, the scattered beam 5 for the direction of observation and the sample 4 (FIG. 1). The z axes of $S_i$ and $S_s$ and chosen to be directed along the direction of the propagation of light.

$v^i$ and $v^s$ are the two-dimensional Jones vectors of the incident and the scattered electric field respectively, formed from the first two components of $E^i$ and $E^s$ correspondingly expressed in $S_i$ and $S_s$ (the third components being identically zero for the particular choice of $S_i$ and $S_s$) and J is the 2×2 Jones matrix of the sample 4 given by:

$$J = F_s R_s^{-1} R R_i F_i \quad (7)$$

where $R_i$ and $R_s$ are the orthogonal transformation matrices bringing $S_i$ and $S_s$ into S, the sample 4 coordinates system in which the Raman tensor R is represented. Under the plane-wave approximation and supposing the sample 4 refractive index equal to that of the ambient, the two matrices $F_i$ and $F_s$ in Eq. (7) take the following simple forms:

$$F_i = \begin{bmatrix} 1 & 0 \\ 0 & 1 \\ 0 & 0 \end{bmatrix} \text{ and } F_s = \begin{bmatrix} 1 & 0 & 0 \\ 0 & 1 & 0 \end{bmatrix} \quad (8)$$

The reader will easily notice that the two transformation matrices $R_i$ and $R_s$ can be conveniently constructed as two products of three Euler-angle orthogonal matrices bringing $S_i$ and $S_s$ into S for the particular scattering geometry used in the experiment.

If the sample 4 consists of many scatterers forming a scattering ensemble (e.g. gaseous or solid multiphonon sample 4), the Raman scattered light is generally only partially polarized and the Jones formalism (6) should be replaced by the more general Mueller-Stokes one [K. Kim, L. Mandel and E. Wolf, J. Opt. Soc. Am. A 4, 433 (1987)]:

$$s^s = M s^i \quad (9)$$

where $s^i$ and $s^s$ are the Stokes vectors of the incident 2 and scattered 5 light respectively and M is the Mueller matrix of the scattering ensemble given by $$M = A \sum_k (J_k \times J_k^*) A^{-1} \quad (10)$$

in the crystalline material case or by:

$$M = A (J \times J^*) A^{-1} \quad (11)$$

in the amorphous or liquid material case (the symbol "x" stands for the Kronecker product of matrices and the asterisk denotes the complex conjugate). The expressions (10) and (11) have been constructed following the general definition of the Mueller matrix given by [K. Kim, L. Mandel and E. Wolf, J. Opt. Soc. Am. A 4, 433 (1987)]. The transformation matrix A is given by [R. M. A. Azzam and N. M. Bashara, *Ellipsometry and Polarized Light*, p. 148 (North Holland, Amsterdam, 1977)]:

$$A = \begin{bmatrix} 1 & 0 & 0 & 1 \\ 1 & 0 & 0 & -1 \\ 0 & 1 & 1 & 0 \\ 0 & i & -i & 0 \end{bmatrix} \quad (12)$$

where i is the imaginary unit.

In component form the Mueller matrix M [R. M. A. Azzam and N. M. Bashara, *Ellipsometry and Polarized Light*, p. 148 (North Holland, Amsterdam, 1977)] of a single scatterer reads:

$$M = \begin{bmatrix} \frac{1}{2}(|J_{11}|^2 + |J_{22}|^2 + |J_{12}|^2 + |J_{21}|^2) & \frac{1}{2}(|J_{11}|^2 - |J_{22}|^2 - |J_{12}|^2 + |J_{21}|^2) & \mathrm{Re}(J_{11}^* J_{12} + J_{21}^* J_{22}) & -\mathrm{Im}(J_{11}^* J_{12} + J_{21}^* J_{22}) \\ \frac{1}{2}(|J_{11}|^2 - |J_{22}|^2 + |J_{12}|^2 - |J_{21}|^2) & \frac{1}{2}(|J_{11}|^2 + |J_{22}|^2 - |J_{12}|^2 - |J_{21}|^2) & \mathrm{Re}(J_{11}^* J_{12} - J_{21}^* J_{22}) & \mathrm{Im}(-J_{11}^* J_{12} + J_{21}^* J_{22}) \\ \mathrm{Re}(J_{11}^* J_{21} + J_{12}^* J_{22}) & \mathrm{Re}(J_{11}^* J_{21} - J_{12}^* J_{22}) & \mathrm{Re}(J_{11}^* J_{22} + J_{12}^* J_{21}) & \mathrm{Im}(-J_{11}^* J_{22} + J_{12}^* J_{21}) \\ \mathrm{Im}(J_{11}^* J_{21} + J_{12}^* J_{22}) & \mathrm{Im}(J_{11}^* J_{21} - J_{12}^* J_{22}) & \mathrm{Im}(J_{11}^* J_{22} + J_{12}^* J_{21}) & \mathrm{Re}(J_{11}^* J_{22} - J_{12}^* J_{21}) \end{bmatrix} \quad (13)$$

In the case of a scattering ensemble (or of multiple scatterers) all products $J_{kl} J_{mn}^*$ should be space averaged (or summed over the number of scatterers).

The Mueller-Stokes formalism, Eqs. (9-11), also allows taking into account partially polarized or unpolarized incident light and therefore, can be considered as a generalization of Placzek formalism, Eqs. (1-3). It is the most suitable framework for the polarimetric Raman experiment, exposed here.

The polarimetric Raman system should be regarded as the generalization of the conventional polarized Raman as well as of ROA systems, in the same way as the Mueller-Stokes formalism generalizes the Placzek formalism.

Actually, by combining four independent input states $e^i$ with four other independent output ones $e^s$, one is capable to obtain sixteen intensity measurements from which the Raman tensor R can be partially or totally retrieved, if desired. It should be noted that for a number of applications, partial information only about the tensor is sufficient.

Thus, by performing polarimetric Raman, one is able to obtain the complete polarization characteristics of the sample, while polarized (or "depolarized") Raman or ROA experiments provide only partial information on the polarization characteristics of the sample.

The polarimetric Raman system may be generally divided into two categories according the implementation of the PSG 7 (or the PSA 8), those using mechanically rotated retarders with fixed retardances and those using mechanically fixed retarders with variable (most often electrically adjustable) retardances.

To the first category there belong devices based on quarter-wave and other fixed retardance plates, as well as on Fresnel rhombs, while the second category comprises devices using voltage-controlled liquid crystal retarders, Pockels cells, photoelastic modulators and more generally, any variable retarders based on electron, magneto- or acousto-optic effects.

Figure 4:
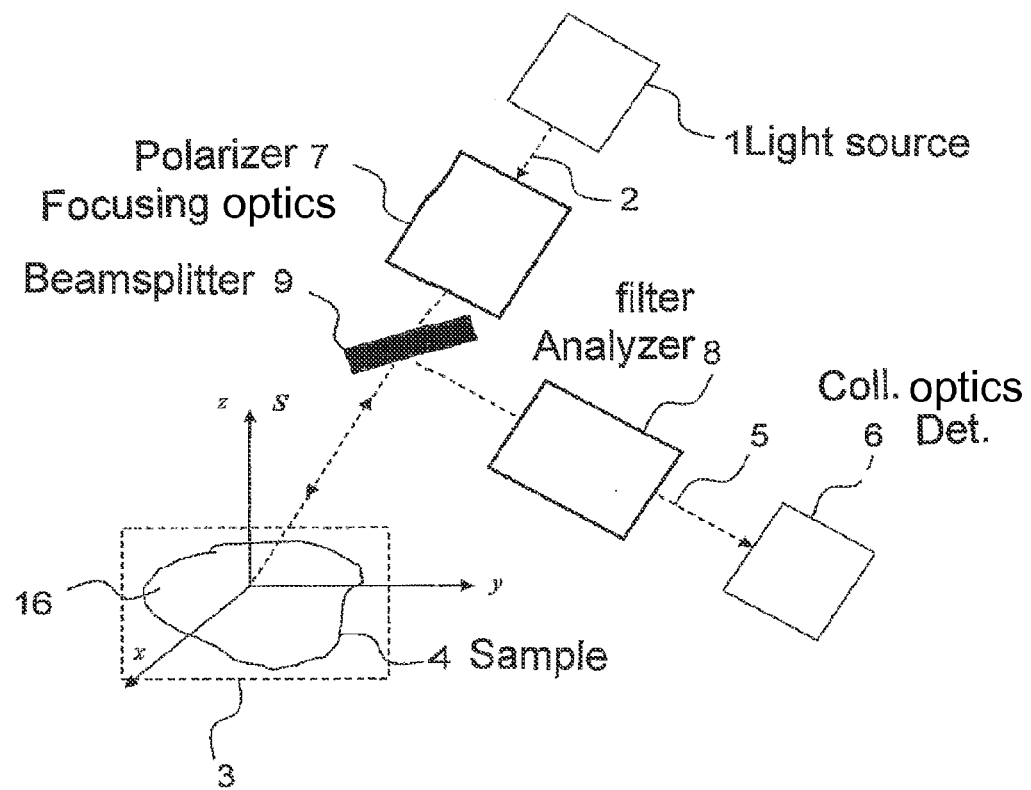
FIG. 4 represents the polarimetric Raman system used in a backscattering configuration according to one particular embodiment of the invention.

According to a particular embodiment of the invention, the polarimetric Raman system can be used in a backscattering configuration, represented in FIG. 4.

The polarimetric Raman system comprises a beamsplitter 9 located between the PSG 7 and the sample 4. The incident light beam 2 passes through the beamsplitter 9 before being backscattered by the sample 4, generating a backRaman scattered light beam 10 which is reflected by the beamsplitter 9 before passing through the PSA 8.

There is a non-exhaustive list of typical applications of Raman spectroscopy to which the polarimetric Raman system may be potentially applied with success. The invention can be also implemented in other specific Raman applications not described below, such as non-linear Raman scattering experiments, for example.

1) Conventional Raman Scattering.

In conventional (i.e., performed on optically inactive materials) Raman spectroscopy far from resonance the Raman tensor R is real symmetric since it is simply proportional to the Raman polarizability tensor α. In a "classical" polarized Raman device the "depolarization ratios" ρ defined as [D. A. Long, *Raman Spectroscopy*, pp. 28; 126; 120 (McGraw Hill, New York, 1977)]:

$$\rho = \frac{{}^{\text{II},\perp}I_{\text{II},\perp}}{{}^{\text{II},\perp}I_{\perp,\text{II}}} \qquad (14)$$

are currently determined. In the above expression the left superscript and the subscript refer to respectively, the polarization state of the incident 2 and the scattered 5 radiation, with the symbols II and ⊥ denoting linear polarizations respectively parallel and perpendicular to the scattering plane and I is the intensity of the scattered radiation.

It is clear that by the experimental determination of the depolarization ratios alone, one cannot get complete information about the components of the Raman tensor R.

Unlike polarized Raman experiment, polarimetric Raman is capable of completely determining the six independent components of the tensor R by using the sixteen (or less when sufficient) polarimetric measurements.

2) Raman Optical Activity (ROA)

In the presence of Raman optical activity in the material under analysis, the Raman tensor R, besides from the Raman polarizability tensor α, contains also contributions from the magnetic dipole and electric quadrupole optical activity tensors G and A, respectively. Since the G and A tensors are purely imaginary in the absence of external magnetic fields, the Raman tensor R becomes generally complex [D. A. Long, *Raman Spectroscopy*, pp. 28; 126; 120 (McGraw Hill, New York, 1977)]. The expression of the Raman tensor becomes (in component form) [L. A. Nafie and D. Che, in *Modern Non-linear Optics*, part 3, p. 105 (Advances in Chemical Physics Series, vol. LXXXV, M. Evans and S. Kielich eds., John Wiley & Sons, New York, 1994)]

$$R_{ij} = \alpha_{ij} + \frac{1}{c}\sum_k \left( \sum_l \varepsilon_{klj} n_l^i G_{ik} + \frac{1}{3}\omega_0 n_k^i A_{ikj} \right) \qquad (15)$$

where $\epsilon_{ijk}$ is the Levi-Cività symbol, $\omega_0$ and $n^i$, the frequency and the propagation unit vector of the incident radiation and c, the speed of light in vacuum.

In the polarimetric picture, the elements $M_{ij}$ of the Mueller matrix M corresponding to the Raman tensor R represent linear combinations of terms of the type $R_{ij} R_{kl}^*$ (which are, moreover, space averaged in the case of amorphous and liquid samples), see Eqs. (7), (10-11) and (13).

The six elements $M_{01}$, $M_{02}$, $M_{03}$, $M_{30}$, $M_{31}$ and $M_{32}$ of the last row and column of M are, by definition, proportional to the imaginary parts of the above terms, see Eq. (13), and will therefore, be zero in conventional Raman and respectively, non-zero in the presence of ROA.

If measured by using polarimetric Raman, they can provide full characterization of the ROA properties of the material under analysis.

Unlike polarimetric Raman, conventional ROA measurements determine only the so called "circular intensity difference ratio" (CID) defined as [L. D. Barron, M. P. Bogaard and A. D. Buckingham, J. Am. Chem. Soc. 95, 603 (1973)]:

$$CID = \frac{{}^R I - {}^L I}{{}^R I + {}^L I} \qquad (16)$$

Here, the left subscripts R and L refer to, respectively, right and left circularly polarized incident light and I is the intensity of the Raman scattered light, possibly analysed with an analyser. It is easy to see that the CID defined above is equal to the normalized Mueller matrix element $M_{03}$ (i.e., to $M_{03}/M_{00}$). It is also clear that the only knowledge of CID can provide only partial information about the tensors α, G and A.

On the contrary, polarimetric Raman is potentially capable of providing extra information on the ROA tensors by determining all Mueller matrix ROA elements instead of just one.

3) Mechanical Stress Characterization Using Raman Spectroscopy

The measurement of only three frequency shifts imposes the use of simplifying hypotheses on the symmetry properties of the stress tensor σ, generally having six independent components, in order to reduce the number of unknown parameters.

By using polarimetric Raman configuration it is possible to fully characterize the modified Raman tensors and therefore, to achieve complete determination of the stress tensor σ without the need for hypotheses on its symmetry properties.

The Raman tensors $R_i$, i=1, 2, 3, of the three degenerate phonon modes at 521 cm$^{-1}$ in unstrained silicon, commonly denoted by $\Delta_i$, have the following forms in the canonical basis [I. de Wolf, H. E. Maes and S. K. Jones, J. Appl. Phys. 79, 7148 (1996)]:

$$\Delta_1 = \begin{bmatrix} 0 & 0 & 0 \\ 0 & 0 & 1 \\ 0 & 1 & 0 \end{bmatrix} \Delta_2 = \begin{bmatrix} 0 & 0 & 1 \\ 0 & 0 & 0 \\ 1 & 0 & 0 \end{bmatrix} \Delta_3 = \begin{bmatrix} 0 & 1 & 0 \\ 1 & 0 & 0 \\ 0 & 0 & 0 \end{bmatrix} \qquad (17)$$

Under the action of stress, the three Raman tensors are modified in accordance with the following relationship valid under the small-strain approximation [G. H. Loechelt, N. G. Cave and J. Menéndez, J. Appl. Phys. 86, 6164 (1999)]:

$$R_k = \sum_i d_{ki} \Delta_i \qquad (18)$$

with $d_{ki}$ being the i-th component of the k-th unit vector $d_k$ (k=1, 2, 3) of the strained basis (the unstrained basis is supposed to coincide with the canonical basis). Since the strained basis may be considered as simply rotated with respect to the unstrained one (because of the orthogonality of the vectors $d_k$, see below), its basis vectors $d_k$ can be, for instance, expressed in terms of the three Euler angles φ, ψ, θ describing the effective rotation (or of any other three conveniently chosen independent parameters).

The vectors $d_k$ appear to be simply the eigenvectors of the matrix K:

$$K = \begin{bmatrix} p\varepsilon_{11} + q(\varepsilon_{22}+\varepsilon_{33}) & 2r\varepsilon_{12} & 2r\varepsilon_{13} \\ 2r\varepsilon_{21} & p\varepsilon_{22} + q(\varepsilon_{11}+\varepsilon_{33}) & 2r\varepsilon_{23} \\ 2r\varepsilon_{31} & 2r\varepsilon_{32} & p\varepsilon_{33} + q(\varepsilon_{11}+\varepsilon_{22}) \end{bmatrix} \quad (19)$$

where $\varepsilon$ is the strain tensor and p, q and r are the so-called deformation potential constants, tabulated for most crystalline materials of interest [E. Anastassakis, in *Light Scattering in Semiconductor Structures and Materials*, p. 173 (D. J. Lockwood and J. F. Young eds., Plenum, New York, 1991)].

Since the matrix K is real symmetric (because of the symmetry of the strain tensor $\varepsilon$), its eigenvectors $d_k$ are orthogonal and its eigenvalues $\lambda_k$ real. The eigenvalues $\lambda_k$ of K relate the degenerated frequency $\omega_0$ to the shifted phonon frequencies $\omega_k$:

$$\lambda_k = \omega_k^2 - \omega_0^2 \quad (20)$$

Finally, the stress tensor $\sigma$ is related to the strain tensor $\varepsilon$ through Hooke's law:

$$\varepsilon = c\sigma \quad (21)$$

where c is the fourth-rank compliance tensor, supposed to be known for the studied material.

As can be readily seen from Eqs. (7), (10) and (18), the Mueller matrix M of the three modified Raman phonon modes under observation will necessarily contain the expression:

$$\sum_k I_k (R_k \times R_k) = \sum_k I_k \sum_{i,j} d_{ki} d_{kj} (\Delta_i \times \Delta_j) = \sum_{i,j} A_{ij} (\Delta_i \times \Delta_j) \quad (22)$$

where $A_{ij}$ are the components of the matrix A given by the expression $$A = \sum_k I_k d_k d_k^T \quad (23)$$

where $I_k$ is the Lorentz lineshape factor of the k-th phonon mode having frequency $\omega_k$ and linewith $\Gamma_k$ [G. H. Loechelt, N. G. Cave and J. Menéndez, J. Appl. Phys. 86, 6164 (1999)]:

$$I_k = \frac{\omega_k \Gamma_k}{(\omega - \omega_k)^2 + \Gamma_k^2} \quad (24)$$

with $\omega$ being the Raman shift spectroscopic frequency.

The matrix A can be experimentally determined at each Raman frequency $\omega$ by fitting the sixteen (or less, if sufficient) polarimetric Raman measurements to the elements of the Mueller matrix M dependent on A through Eq. (22).

It is clear that the complete experimental determination of the matrix A in terms of the three phonon frequencies $\omega_k$ as well as of the three Euler angles $\varphi$, $\psi$, $\theta$ (or of any other three conveniently chosen equivalent parameters) contained in $d_k$ will provide a total of six independent parameters, in theory allowing for the unambiguous determination of the six independent components of the general symmetric stress tensor $\sigma$ by reconstructing the matrix K from its eigenvalue-eigenvector decomposition:

$$K = \sum_k \lambda_k d_k d_k^T \quad (24)$$

and by using Eqs. (19-21). On the contrary, the experimental determination of the three phonon frequencies only is clearly insufficient to resolve the general case.

The complete experimental determination of the matrix A can be readily achieved in a polarimetric Raman experiment and, moreover, without the need for sample rotation.

4) Far-Field Compensation in Tip-Enhanced Raman Spectroscopy (TERS)

In some particular applications, such as the far-field compensation in tip-enhanced Raman spectroscopy (TERS), the use of a PSG 7 or a PSA 8 only (possibly coupled with an analyser 18 and a polarizer 17 respectively) may be sufficient.

Figure 5:
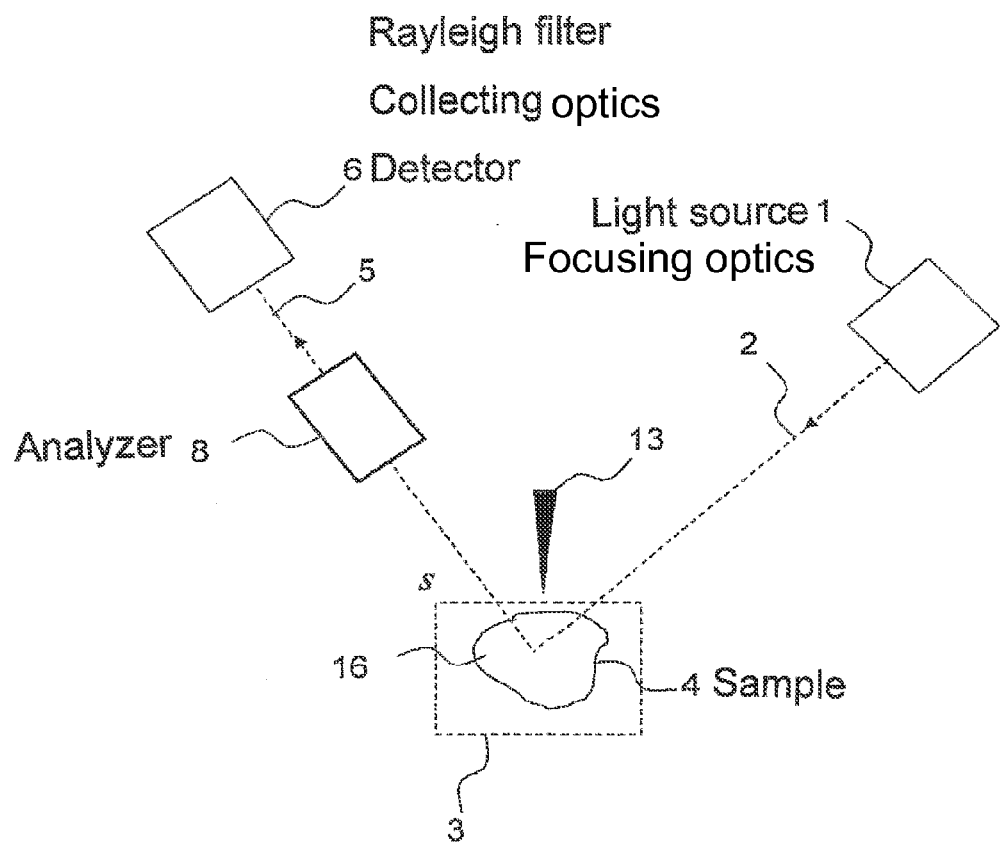
FIG. 5 represents a polarimetric TERS configuration comprising only a PSA according to one particular embodiment of the invention.
Figure 6:
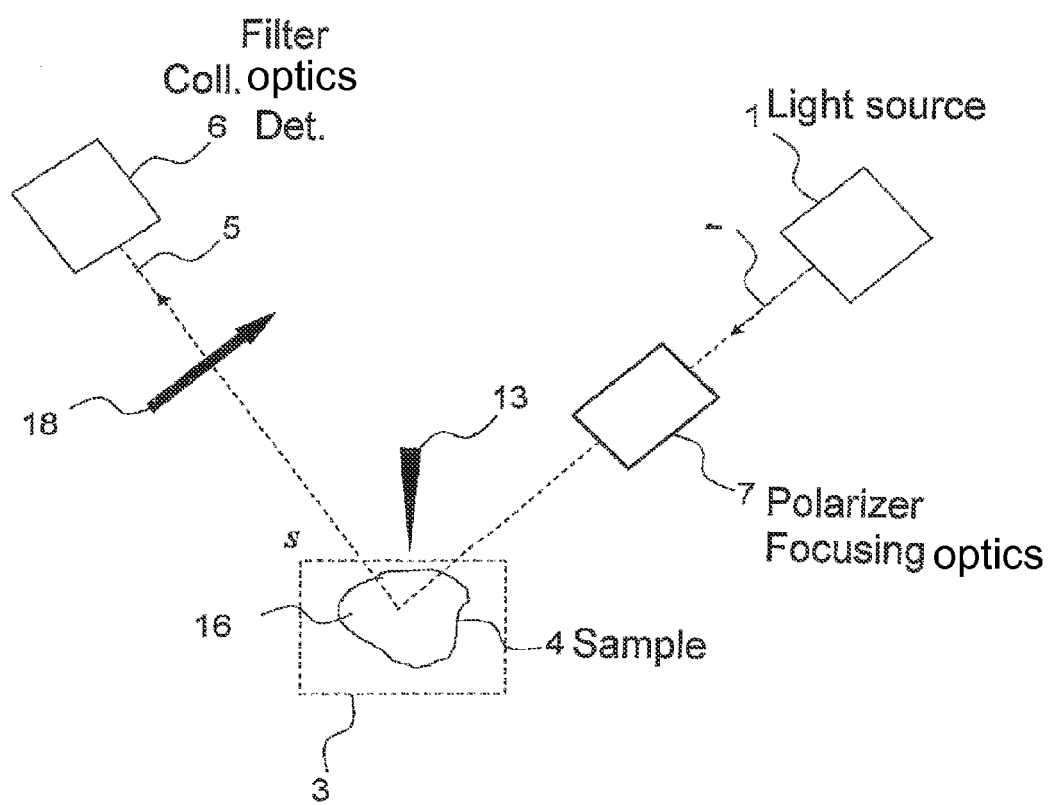
FIG. 6 represents a polarimetric TERS configuration comprising a PSG and an analyser according to one particular embodiment of the invention.

FIGS. 5 and 6 represent polarimetric TERS configuration examples.

The polarimetric TERS system comprises an excitation source 1 emitting an incident light beam 2 and a sample holder 3, on which the sample 4 can be mounted. The incident light beam 2 is focused on the sample 4 to generate a Raman scattered light. Means for collecting the Raman scattered light able to form a Raman scattered light beam 5.

It comprises a detection system 6 measuring the intensity of the Raman scattered light beam 5 in function of time and optics to focus the incident light beam 2 onto the sample surface 16.

In this case, the PSG 7 (or PSA 8) is not used to generate four independent polarization states, but rather to achieve an arbitrary polarization state.

Tip-enhanced Raman spectroscopy (TERS) consists in exciting and recording the near-field contribution to the scattered Raman field by bringing a sharp tip 13 (having about a 50-nm radius) in contact with (or very close to) the incident beam spot at the surface under analysis [A. Hartschuh, M. R. Beversluis, A. Bouhelier and L. Novotny, Phil. Trans. Roy. Soc. Lond. A 362, 807 (2004)].

In TERS, one of the main instrumental problems is the discrimination between the near field contribution to the total field (tip in contact with the sample) and the far field (tip withdrawn).

In order to get a higher contrast between the near field and the far field (generally defined as the ratio "total field intensity over far field intensity") and therefore, a higher near field contribution, it is obviously desirable to reduce the far field to the minimum.

To do so, an analyser 18 is usually inserted in the scattered beam 5 (see FIG. 6) and set to an azimuth such that the far field (with the tip 13 withdrawn) is a minimum [V. Poborchii, T. Tada and T. Kanayama, Japanese J. Appl. Phys. 44, L202 (2005)]. The incident beam 2 is supposed to be totally polarized, as is always the case in practice either because of the use of a polarizer or because of the polarized nature of the exciting laser radiation.

However, it is clear that a total compensation of the far field can be achieved in the above way only if the Raman scattered light 5 is totally and, moreover, linearly polarized which is not the case in general.

If the scattered radiation 5 is totally but not linearly polarized, a total compensation can still be obtained by replacing the analyser 18 by a PSA 8.

The same result can be also obtained by inserting a PSG 7 in the incident beam 2 and keeping the analyser 18 at the output (configuration denoted by "PSG+A").

However, if the scattered radiation 5 is only partially polarized as is the case, for instance, when multiple phonons are observed or when a partially polarized incident light 2 is used, the use of a PSA 8 (or of PSG+A) cannot compensate the far-field intensity (i.e., the $s_0$ component of the Stokes vector $s^s$ of the Raman scattered light).

It remains possible in this case, however, to compensate totally the $s_1$ or the $s_2$ components of the Stokes vector of the Raman scattered light (the $s_3$ component is identically zero for optically inactive materials and linearly polarized incident light) and thus, to maximize the contrast, by using a PSA 8 (PSG 7).

In FIG. 5, the polarimetric TERS system comprises only a PSA 8 in the scattered beam 5 which can compensate the total far field intensity ($s_0$ Stokes parameter) if the Raman scattered light is totally polarized, and $s_1$ or $s_2$ Stokes parameters of the far field if the Raman scattered light is partially polarized.

In another possible embodiment, the polarimetric TERS system can comprise a PSA 8 and a polarizing component such a polarizer 17 or a half-wave plate, without limitation.

FIG. 6 represents a polarimetric TERS system comprising a PSG 7 in the incident beam 2 and an analyser 18 in the scattered beam 5 which can compensate the total far field intensity ($s_0$ Stokes parameter) if the Raman scattered light is totally polarized.

This application of polarimetric Raman is summarized in the following table:

| polarization of the Raman scattered light | total | partial |
|---|---|---|
| polarimetric implementation compensated quantity | PSA or PSG + A $s_0$ (= intensity) | PSA $s_1$ or $s_2$ |

The possible compensation strategies in TERS are functions of the degree of polarization of the Raman scattered light.

5) Resonance Raman Scattering

As mentioned in 1), the Raman tensor R, being proportional to the Raman polarizability tensor $\alpha$, is real symmetric if the frequency of the incident light 2 is far from the electronic transition frequencies (absorption bands) of the material.

However, if the frequency of the incident light 2 is close to an electronic transition frequency (i.e., is in a close-to-resonance condition), the tensor $\alpha$ (and therefore R, too) becomes generally complex asymmetric. In the absence of magnetic fields, the tensor $\alpha$ remains real and can be decomposed as a sum of a symmetric and an antisymmetric term, $\alpha = \alpha_s + \alpha_a$ [D. A. Long, *Raman Spectroscopy*, pp. 28; 126; 120 (McGraw Hill, New York, 1977)].

The antisymmetric term $\alpha_a$ adds three more components to the six components of the symmetric term $\alpha_s$. Clearly, the complete determination of the Raman tensor R and therefore of $\alpha$ in terms of its nine independent components can be achieved only by performing a polarimetric Raman experiment.

It should be underlined that polarimetric Raman technique, as described above, is totally different in its principle from the simple opto-mechanical coupling of a Raman spectrometer and a polarimeter or an ellipsometer, even if a common light source possibly including a PSG is used for both of them.

In polarimetric Raman, it is the Raman frequency-shifted scattered radiation that is analysed by the PSA, while in "classic" polarimetry it is the radiation specularly reflected on the sample and having the same frequency as the incident radiation that is analysed.

Similarly, the polarimetric Raman technique is fundamentally different from the two-state polarization modulation techniques currently used in ROA device. In a polarimetric Raman system there is either a consecutive generation of four independent polarization states or a single generation of an arbitrary polarization state (the latter in the case of far-field compensation in tip-enhanced Raman spectroscopy, see section 4)).

The invention claimed is:

1. A polarimetric Raman system for analysing a sample (4) comprising:
    an excitation source (1) emitting an incident light beam (2), said excitation source (1) being configured for producing a Raman scattered light having an intensity,
    a sample holder (3), on which the sample (4) can be mounted,
    means for focusing the incident light beam (2) onto the sample surface (16) to generate the Raman scattered light,
    means for collecting the Raman scattered light and filtering it from Rayleigh scattered light to form a Raman scattered light beam (5),
    a detection system (6) measuring intensity of the Raman scattered light beam (5) as a function of time, and
    at least a polarization state generator (PSG) (7) able to produce four independent polarization states or a polarization state analyser (PSA) (8) able to analyse four independent polarization states in order to detect the intensity of the Raman scattered light beam (5) making it possible to calculate a partial or complete Mueller-Stoke matrix of the sample (4), the incident light beam (2) passing through said PSG (7) before being scattered by the sample (4) and the Raman scattered light beam (5) passing through said PSA (8) after being scattered by the sample (4).

2. A polarimetric Raman system according to claim 1, comprising the PSG (7) working with the PSA (8), said PSG (7) being able to generate four independent polarization states and said PSA (8) being able to analyse four independent polarization states making it possible to obtain a partial or complete Mueller-Stokes matrix of the sample (4) comprising 16 elements.

3. A polarimetric Raman system according to claim 2, further comprising a beamsplitter (9) located between the PSG (7) and the sample (4), the incident light beam (2) passing through said beamsplitter (9) before being backscattered by the sample (4), generating a Raman backscattered light beam (10) reflected by the beamsplitter (9) before passing through the PSA (8).

4. A polarimetric Raman system according to claim 1, with only the PSA (8), the Raman scattered light beam (5) passing through said PSA (8) after being scattered by the sample (4).

5. A polarimetric Raman system according to claim 1, comprising the PSA (8) and a polarizing component, the incident light beam (2) passing through said polarizing component before being scattered by the sample (4) and the Raman scattered light beam (5) passing through said PSA (8) after being scattered by the sample (4).

6. A polarimetric Raman system according to claim 1, comprising the PSG (7) and an analyser (12), the incident light beam (2) passing through said PSG (7) before being scattered by the sample (4) and the Raman scattered light beam (5) passing through said analyser (12) after being scattered by the sample (4).

7. A polarimetric Raman system according to claim 4, further comprising a sharp tip (13) suitable for tip-enhanced Raman spectroscopy (TERS), said sharp tip (13) being very close or in contact with the incident light spot at the surface (16) of the sample and exciting the near-field contribution to the scattered Raman field.

8. A polarimetric Raman method for analysing a sample (4) wherein:
- an incident light beam (2) adapted for producing a Raman scattered light having an intensity is generated,
- the incident light beam (2) is focused onto the sample surface (16) to generate the Raman scattered light,
- the Raman scattered light is collected and filtered from Rayleigh scattered light to form a Raman scattered light beam (5),
- intensity of the Raman scattered light beam (5) is measured as a function of time,
- four independent polarization states of the incident light beam (2) before being scattered by the sample (4) are generated and/or four independent polarization states of the Raman scattered light beam (5) after being scattered by the sample (4) are analysed in order to detect the intensity of the Raman scattered light beam (5) making it possible to calculate a partial or complete Mueller-Stokes matrix of the sample (4).

9. A polarimetric Raman method according to claim 8, characterised in that four independent polarization states of the incident light beam (2) are generated and in that four independent polarization states of the Raman scattered light beam (5) are analysed consecutively for each independent polarization states of the incident light beam (2) generated making it possible to obtain a complete or partial Mueller-Stokes matrix of the sample (4) comprising 16 elements.

10. A polarimetric Raman method according to claim 9, characterised in that the incident light beam (2) passes through a beamsplitter (9) before being backscattered by the sample (4), generating a Raman backscattered light beam (10), four independent polarization states of the Raman backscattered light beam (10) being analysed after the reflection of the Raman backscattered light beam (10) on the beamsplitter (9).

11. A polarimetric Raman method according to claim 8, wherein the method is applied to tip-enhanced Raman spectroscopy (TERS) wherein the near-field contribution to the scattered Raman field is measured.

12. A polarimetric Raman system according to claim 5, further comprising a sharp tip (13) suitable for tip-enhanced Raman spectroscopy (TERS), said sharp tip (13) being very close or in contact with the incident light spot at the surface (16) of the sample and exciting the near-field contribution to the scattered Raman field.

13. A polarimetric Raman system according to claim 6, further comprising a sharp tip (13) suitable for tip-enhanced Raman spectroscopy (TERS), said sharp tip (13) being very close or in contact with the incident light spot at the surface (16) of the sample and exciting the near-field contribution to the scattered Raman field.

* * * * *